United States Patent
Chakramakkil et al.

(10) Patent No.: US 11,813,008 B2
(45) Date of Patent: Nov. 14, 2023

(12)
(54) MEDIAL TROCHANTERIC PLATE FIXATION

(71) Applicant: Howmedica Osteonics Corp., Mahwah, NJ (US)

(72) Inventors: Keith Chakramakkil, Mumbai (IN); Haley Prout, Hoboken, NJ (US); Don Imami, Hoboken, NJ (US); Erika Corbin, Mahwah, NJ (US); Sheldon Nidhan, Livingston, NJ (US); Rachel Gibbons, Easton, PA (US); Matthew P. Abdel, Rochester, MN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 111 days.

(21) Appl. No.: 17/313,402

(22) Filed: May 6, 2021

(65) Prior Publication Data
US 2021/0369310 A1    Dec. 2, 2021

Related U.S. Application Data

(60) Provisional application No. 63/029,795, filed on May 26, 2020.

(51) Int. Cl.
| | | |
|---|---|---|
| *A61B 17/88* | (2006.01) | |
| *A61B 17/74* | (2006.01) | |
| *A61B 17/80* | (2006.01) | |
| *A61B 17/84* | (2006.01) | |
| *A61B 17/82* | (2006.01) | |

(52) U.S. Cl.
CPC ............. *A61B 17/88* (2013.01); *A61B 17/74* (2013.01); *A61B 17/809* (2013.01); *A61B 17/8061* (2013.01); *A61B 17/82* (2013.01); *A61B 17/842* (2013.01)

(58) Field of Classification Search
CPC ..... A61B 17/74; A61B 17/80; A61B 17/8004; A61B 17/8061; A61B 17/808; A61B 17/82; A61B 17/842; A61B 17/88; A61B 17/8861
See application file for complete search history.

(56) References Cited

U.S. PATENT DOCUMENTS

| | | | |
|---|---|---|---|
| 4,269,180 A | 5/1981 | Dall et al. | |
| 5,324,291 A | 6/1994 | Ries et al. | |
| 5,741,259 A * | 4/1998 | Chan .................. | A61B 17/8042 606/103 |

(Continued)

FOREIGN PATENT DOCUMENTS

JP    H09168548 A    6/1997

OTHER PUBLICATIONS

US 9,597,139 B2, 03/2017, Cavallazzi (withdrawn)
(Continued)

*Primary Examiner* — Larry E Waggle, Jr.
(74) *Attorney, Agent, or Firm* — Lerner David LLP (57) ABSTRACT

A method of bone fixation includes placing a bone plate adjacent to a lesser trochanter on a medial aspect of a femur such that at least a portion of the lesser trochanter is positioned between appendages of the bone plate, wrapping cables coupled to the bone plate about a first and second bone fragment of a proximal femur, and tightening the cables to secure the first and second bone fragments together.

20 Claims, 11 Drawing Sheets

(56) References Cited

U.S. PATENT DOCUMENTS

| | | | |
|---|---|---|---|
| 5,797,916 A | | 8/1998 | McDowell |
| 5,941,881 A | | 8/1999 | Barnes |
| 6,066,141 A | | 5/2000 | Dall et al. |
| 6,139,550 A | * | 10/2000 | Michelson ............. A61B 17/80 606/295 |
| 6,872,210 B2 | | 3/2005 | Hearn |
| 7,207,993 B1 | * | 4/2007 | Baldwin ................ A61B 17/74 606/65 |
| 7,250,054 B2 | | 7/2007 | Allen et al. |
| 7,255,701 B2 | | 8/2007 | Allen et al. |
| 8,764,809 B2 | * | 7/2014 | Lorenz .................. A61B 17/74 606/283 |
| 9,101,426 B2 | * | 8/2015 | Forderer ............... A61B 17/80 |
| 9,138,267 B2 | | 9/2015 | Cavallazzi |
| 9,138,268 B2 | | 9/2015 | Cavallazzi et al. |
| 9,138,269 B2 | | 9/2015 | Cavallazzi et al. |
| 9,241,748 B2 | | 1/2016 | Bernstein et al. |
| 9,333,021 B2 | | 5/2016 | Gephart |
| 9,421,050 B2 | | 8/2016 | Bernstein et al. |
| 9,439,697 B2 | | 9/2016 | Mebarak et al. |
| 9,561,064 B2 | | 2/2017 | Goodwin et al. |
| 9,649,118 B2 | | 5/2017 | Mebarak |
| 9,724,142 B2 | * | 8/2017 | Park .................... A61B 17/8061 |
| 10,426,532 B2 | | 10/2019 | Goodwin et al. |
| 2006/0057895 A1 | | 3/2006 | Fujita et al. |
| 2006/0235401 A1 | | 10/2006 | Baldwin et al. |
| 2007/0173815 A1 | * | 7/2007 | Murase ................. A61B 17/15 606/53 |
| 2010/0234896 A1 | | 9/2010 | Lorenz et al. |
| 2014/0243841 A1 | | 8/2014 | Cavallazzi |
| 2017/0209190 A1 | | 7/2017 | Goodwin, Jr. et al. |
| 2019/0201064 A1 | * | 7/2019 | Ananthan .......... A61B 17/8057 |

OTHER PUBLICATIONS

Patel, et al., The Dislocating Hip Arthroplasty—Prevention and TReatment, The Journal of Arthroplasty, Jun. 2007, pp. 86-90, vol. 22, No. 4.

Delaunay et al., What are the Causes for Failures of Primary Hip Arthroplasties in France?, Clinical Orthopaedics and Related Research, Dec. 2013, pp. 3863-3869, vol. 471, No. 12.

Esposito et al., What is the Trouble With Trunnions?, Clinical Orthopaedics and Related Research, Dec. 2014, pp. 3652-3658, vol. 472, No. 12.

Abdel et al., What Safe Zone? The Vast Majority of Dislocated THAs are Within the Lewinnek Safe Zone for Acetabular Component Position, Clinical Orthopaedics and Related Research, Feb. 2016, pp. 386-391, vol. 474, No. 2.

Brown, et al., Hip Arthroplasty: Management Factorials Reconstruction of the hip after resection of periacetabular oncological lesions, The Bone & Joint Journal, Jan. 2018, pp. 22-30, vol. 100-B, No. 1.

Buckland et al., Acetabular Anteversion Changes Due to Spinal Deformity Correction: Bridging the Gap Between Hip and Spine Surgeons, The Journal of Bone and Joint Surgery, Dec. 2015, vol. 97-A, No. 23.

Malkani et al., Total Hip Arthroplasty in Patients With Previous Lumbar Fusion Surgery: Are There More Dislocations and Revisions?, The Journal of Arthroplasty, Apr. 2018, pp. 1189-1193, vol. 33.

McAlister, et al., Two-Stage Revision of Total Hip Arthroplasty for Infection is Associated with a High Rate of Dislocation, The Journal of Bone and Joint Surgery, Feb. 2019, pp. 322-329, vol. 101-A, No. 4.

Hartzler et al., Otto Aufranc Award: Dual-mobility Constructs in Revision THA Reduced Dislocation, Rerevision, and Reoperation Compared With Large Femoral Heads, Clinical Orthopaedics and Related Research, published online Jan. 2018, pp. 293-301.

Goldman, et al., The Lawrence D. Dorr Surgical Techniques & Technologies Award: Why are Contemporary Revision Total Hip Arthroplasties Failing? An Analysis of 2500 Cases, The Journal of Arthroplasty, available online Jan. 2019, pp. S11-S16, vol. 34.

Abdel et al., Epidemiology of periprosthetic femoral fractures in 5417 revision total hip arthroplasties, The Bone and Joint Journal, Apr. 2016, pp. 468-474, vol. 98-B, No. 4.

European Search Report issued in Appln. No. 21172697.1 dated Oct. 18, 2021 (2 pages).

\* cited by examiner

MEDIAL TROCHANTERIC PLATE FIXATION

CROSS-REFERENCE TO RELATED APPLICATIONS

This application claims the benefit of the filing date of U.S. Provisional Application No. 63/029,795, filed May 26, 2020, the disclosure of which is hereby incorporated by reference.

BACKGROUND OF THE INVENTION

Various orthopedic procedures involve the use of wires, cables, and/or plates to secure bone pieces/segments created by a fracturing of bone, such a trochanter of a femur, for example. Such fractures may be intraoperative fractures (e.g., occurring during a hip replacement procedure), post-operative fractures (e.g., periprosthetic fractures), or due to traumatic injury, for example.

In addition, wires, cables, and/or plates may be used to secure bone pieces/segments created by planned surgical cutting, such as an osteotomy. For example, a hip replacement prosthesis may be secured within an intramedullary canal of a proximal femur via cement or bone ingrowth into a porous surface of a press-fit stem. In some instances, a revision procedure, which entails the removal of the previously implanted prosthesis, may be required due to prosthesis wear or loosening, infection, periprosthetic fracture, and the like. In order to remove a securely fixed prosthesis and/or cement mantle from a proximal femur, a trochanteric or extended trochanteric osteotomy may be performed whereby the greater trochanter and, in the case of an extended osteotomy, an extended region of bone inferior to the greater trochanter are resected from the remaining femur in order to expose the prosthesis to facilitate its removal.

In each instance, whether in the case of a fracture or planned cutting, the bone, unless unsalvageable, must be reconstructed and held together, preferably in a compressed manner. In some instances, the bone is reconstructed about a joint prosthesis so that the bone not only heals to itself but also heals in a manner to retain the prosthesis.

Bone reconstruction involving proximal femoral fractures, such as trochanteric fractures, often include the wrapping of cables, such as Dall-Miles cables, about the proximal femur so as to compress and secure the bone pieces to each other and, in some cases, about a portion of a prosthesis. Such cables are sometimes utilized in conjunction with plates. Such plates are often placed on a lateral aspect of the femur with one or more cables coupled to the plate.

However, such plates, which can be bulky and may extend over the greater trochanter and down to the diaphysis of the bone, have a tendency to migrate particularly since several soft tissue structures attach and apply force to the greater trochanter during ambulation. In addition, soft tissue structures that pass over the greater trochanter can rub against the plate during ambulation. Such rubbing may also lead to trochanteric bursitis or other localized soft tissue inflammation. Moreover, plate migration can lead to non-union of the bone pieces which may further result in joint dislocation and periprosthetic joint infection. Thus, further developments are desirable.

BRIEF SUMMARY OF THE INVENTION

The present disclosure describes various bone plates and methods of bone fixation utilizing such bone plates. Such methods generally include the placement of the bone plates in a medial position adjacent to a lesser trochanter of a femur. The bone plates may be initially secured from migration via bone screws and/or bone spikes. The bone plates may also include a roughened/textured surface that can also initially secure the plate during intraoperative placement via friction and can be created via additive manufacturing or by machining the inner surface to obtain the desired surface texture. Two or more cables, such as Dall-Miles cables, may be coupled to the plate and routed about the proximal femur in order to secure bone pieces to each other. The medial positioning of the bone plates reduces incidences of migration, non-fusion, soft tissue irritation, and/or bursitis relative to lateral placement. Migration is also limited via the securement features, such as the bone screws, spikes, tensioned cables and roughened surfaces. Moreover, the shapes of the plates may be such that they can be positioned at least partially about the lesser trochanter such that the protruding nature of the lesser trochanter can help prohibit migration of the plates.

BRIEF DESCRIPTION OF THE DRAWINGS

The features, aspects, and advantages of the present invention will become better understood with regard to the following description, appended claims, and accompanying drawings in which:

DETAILED DESCRIPTION

As used herein unless stated otherwise, the term "proximal" means closer to the heart, and the term "distal" means further from the heart. The term "anterior" means toward the front part of the body or the face, the term "posterior" means toward the back of the body. The term "medial" means closer to or toward the midline of the body, and the term "lateral" means further from or away from the midline of the body. The term "inferior" means closer to or toward the feet, and the term "superior" means closer to or toward the crown of the head. As used herein, the terms "about," "generally," and "substantially" are intended to mean that slight deviations from absolute are included within the scope of the term so modified.

FIGS. 1A-1F depict a fixation plate/implant 10 according to an embodiment of the present disclosure. Fixation plate 10 generally includes a front side or bone contacting side 26, a back side 24 opposite the front side 26, a plate body 20, appendages 30, and a cable protrusion 40.

Figure 1A:
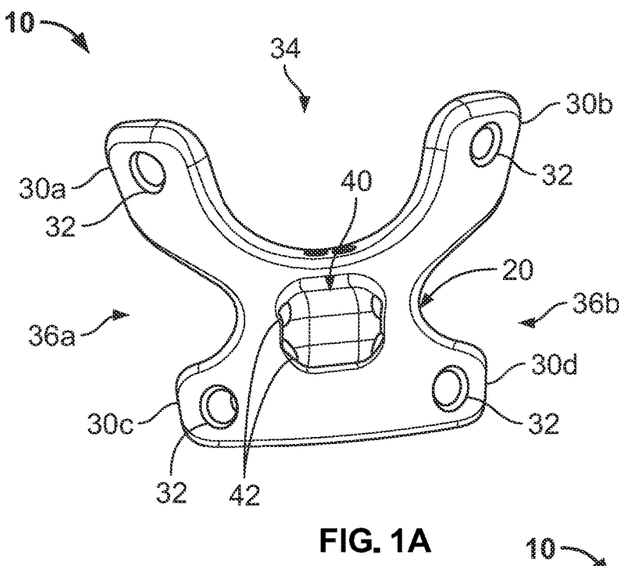
FIG. 1A is a rear perspective view of a fixation plate according to a first embodiment of the present disclosure.
Figure 1B:
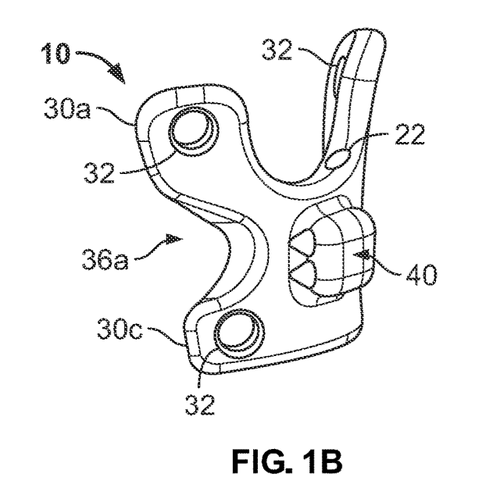
FIG. 1B is a side perspective view of the fixation plate of FIG. 1A.
Figure 1C:
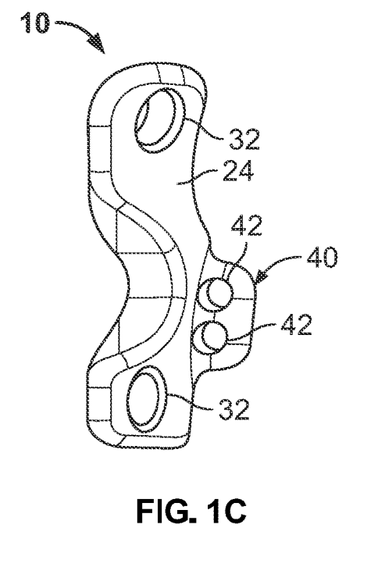
FIG. 1C is a side elevational view of the fixation plate of FIG. 1A.
Figure 1D:
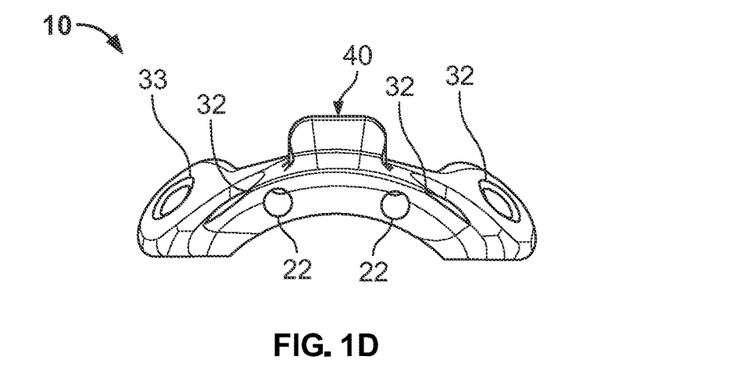
FIG. 1D is a bottom view of the fixation plate of FIG. 1A.

Appendages or arm members 30 extend outwardly from body 20. In the embodiment depicted, plate 10 includes four appendages 30a-d in which a first and second appendage 30a-b are located at a superior end of plate 10, while a third and fourth appendage 30c-d are located at an inferior end of plate 10. First and second appendages 30a-b are generally separated from each other by a superior cut-out or recess 34, which is shown to have a parabolic shape. Similarly, first and third appendages 30a, 30c are separated by a first side cut-out or recess 36a, while second and fourth appendage 30b, 30d are separated by a second side cut-out or recess 36b disposed opposite the first side recess 36a. Such side cut-outs 36a-b are also parabolic in shape but have different dimensions from that of superior cut-out 34. In this regard, superior cut-out 34 is dimensioned so that it can receive and conform to a perimeter of a lesser trochanter of a femur, such as lesser trochanter 52 of bone 50 of FIG. 1F. In other words, plate 10 is intended to lie flush or close to flush against an outer cortex of femur 50 at a location adjacent and generally inferior to lesser trochanter 52. Superior cut-out 34 is shaped and dimensioned to receive at least a portion of lesser trochanter 52 of a patient's bone so that first and second appendages 36a-b cradle lesser trochanter 52 and lie flush against the bone immediately surrounding lesser trochanter 50. Appendages 30a-d also each include a screw hole 32 extending therethrough from back side 24 of plate 10 to front side 26 thereof. Such screw holes 32 are configured to each receive a bone screw for initial securement of plate 10 to bone and may be biased or unbiased screw holes.

Cable protrusion or cable mound 40 extends backwardly from the back side 24 of plate 10 and in particular a back side of body 20. Protrusion 40 defines passageways or channels 42 that extend entirely therethrough. In the embodiment depicted, protrusion 40 includes two passageways 42 that are oriented in a parallel fashion relative to each other. Protrusion 40 is preferably placed over a center of geometry of plate 10 and passageways 42 are preferably located near the center of geometry with one passageway 42 being on an opposite side of the center of geometry from another passageway 42. This central placement of protrusion 40 and passageways 42 minimizes effects from unbalanced cable tensile forces thereby reducing the chances of plate migration from its intended position. Also, more or less passageways 42 are contemplated. For example, plate 10 may include a single passageway 42 through protrusion 40 or may include three or four passageways 42. Passageways 42 are configured to receive cables or wires, such as Dall-Miles cables, therethrough. Protrusion 40 may be crimped by a tool so that passageways 42 are collapsed onto a cable therein in order to secure the cable from loosening. Passageways 42 are aligned with first and second side cut-outs 36a-b such that longitudinal axes of passageways 42 extend over side cut-outs 36a-b. Cut-outs 36a-b extend inwardly toward protrusion 40 and terminate adjacent thereto. In this regard, side cut-outs 36a-b provide clearance for cables extending from passageways 42 such that cables can be wrapped about a bone with minimal impingement from plate 10.

Body 20 is in the form of a plate that has a thickness defined between the back and front sides 24, 26 of plate 10 and, in particular, a bone contacting surface and a back side surface of body 20. Similar to protrusion 40, body 20 also includes passageways or channels 22 that extend entirely therethrough and, in the particular embodiment, a first and second passageway 22. However, such passageways 22 extend vertically in a superior-inferior direction between the bone contacting surface and back side surface of body 20, whereas passageways 42 extend side to side transverse to the superior-inferior direction. In this regard, passageways 22 intersect or, in other words, open up to superior cut-out 34. Passageways 22 may be parallel to each other or may be oriented at various angles relative to each other and may be positioned at various distances from each other. For example, passageways 22 can be angled relative to each other up to about 45 degrees. Moreover, where passageways 22 are angled toward each other, they angle toward each other in an inferior direction such that their point of intersection is located inferior to plate 10.

Figure 1E:
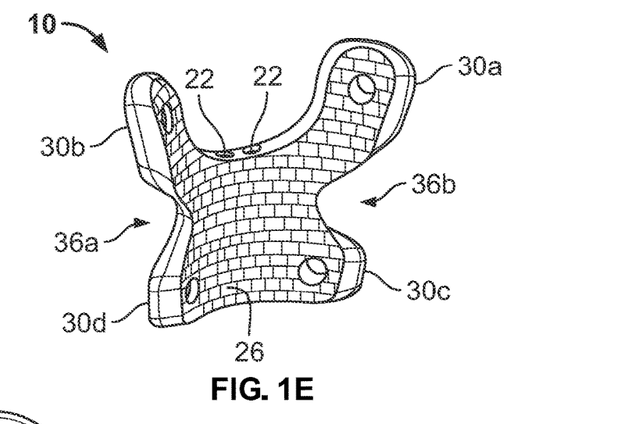
FIG. 1E is a front perspective view of the fixation plate of FIG. 1A.

Front side 26 of plate 10 is a bone contacting side of plate 10 which may include a roughened/textured surface, as best shown in FIG. 1E. Such surface can be produced via additive manufacturing, machining, or grit blasting, for example, so as to produce a desired surface texture and roughness. The roughened surface could be in the form of stippling, corrugations, or a diamond shaped pattern, for example. When positioned against bone cortex, such surface generates friction that helps prevent migration of the plate.

Front side 26 of plate 10 is curved in at least two planes. In particular, front side 26 of plate 10 is concavely curved in a transverse/horizontal plane that intersects plate 10 and bisects it into superior and inferior portions. The superior portion includes arm members 30a-b, and the inferior portion includes arm members 30c-d. Back side 24 of plate 10 is correspondingly convexly curved. The concave curvature of front side 26 also tapers inwardly from a superior end toward an inferior end of plate such that a radius of curvature is greater at the superior end than at the inferior end of plate 10. Front side 26 is also convexly curved in a coronal/vertical plane that is perpendicular to the transverse plane and bisects plate 10 into side portions where a first side portion includes arm members 30a and 30c and a second side portion includes arm members 30b and 30d. Such dual curvature is intended to correspond to the geometry of the proximal femur particularly in the region surrounding the lesser trochanter and primarily inferior to it.

In some embodiments, plate 10 can be bent beyond its initial configuration by a surgeon via a plate bender in situ, such as in trauma scenarios, in order to conform to a patient's specific geometry. In other embodiments, a kit can be provided with multiple plates, like that of plate 10, such that the plates in the kit have differing lengths and widths to account for various patient anatomies and fracture configurations. In even further embodiments, the dual curvature and tapered shape can be matched to a population of femurs in order to obtain a best fit to a particular patient. This may be achieved through an analysis of a bone database. For example, the Stryker® Orthopaedics Modeling and Analytics (SOMA) database may be used to create the geometry of plate 10. The SOMA database contains detailed medical images of thousands of bones from diverse populations of individuals. Geometric data of the bone region in question (i.e., area surrounding and including the lesser trochanter) can be extrapolated from a designated population to which the patient is a part (e.g., a representative sample of bones having the same designated characteristic(s) such as race, gender, height, or a combination thereof). A virtual implant may be overlaid onto a virtual bone image that represents the geometric data extracted from the designated population. The virtual implant may be manipulated either manually within a virtual space by a user or via an automated function that manipulates the virtual implant to conform to the virtual bone in the target area of interest. The final virtual implant, which may have other modifications added to it, such as surface finishes, can then be utilized in manufacturing software, such as software for additive manufacturing, to manufacture the implant in accordance with the generated virtual implant. It should be understood that patient specific versions of plate 10 can be similarly created for a patient's specific and unique geometry, such as via medical images (e.g., CT, MRI, or x-ray images) of the patient's femur.

In addition to that described above and illustrated in the figures, various other operations will now be described. It should be understood that the following operations do not have to be performed in the exact order described below. Instead, various steps may be handled in a different order or simultaneously. Steps may also be omitted or added unless otherwise stated therein.

Figure 1F:
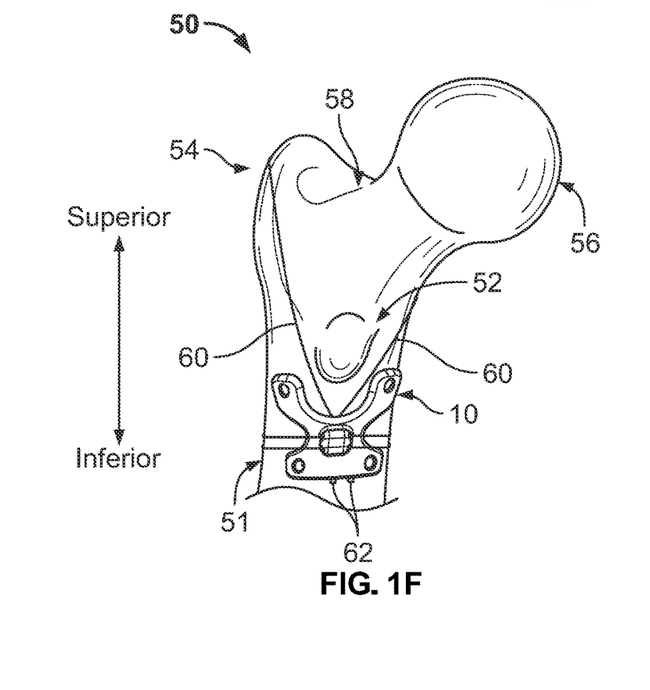
FIG. 1F depicts the fixation plate of FIG. 1A in associate with a proximal femur.

Plate 10 can be utilized to reconstruct bone, such as femur 50, which may be fractured due to injury, such as a fracture of the greater trochanter 54, or segmented due to a surgical intervention, such as a trochanteric osteotomy. It should be understood that the methods described herein can be performed in the context of bone fracture reduction and repair and reconstruction of bone segmentation due to an osteotomy. Proximal femoral osteotomies may be performed to remove a well fixed hip prosthesis and/or bone cement utilized to secure such prosthesis. In this regard, a greater trochanteric osteotomy may be performed to expose portions of the hip prosthesis within an intramedullary canal of the bone 50 such that burrs, osteotomes, and other instruments can be used free the implant from the bone 50. Trochanteric osteotomies can include an extended type in which the greater trochanter 54 and an extended region of bone extending inferior from the greater trochanter 54 down to the femoral diaphysis 54 is resected away from the remaining femur 50. Trochanteric osteotomies that are not of the extended type involve the resection of the greater trochanter 54 but not the extended region inferior to it. Thus, reconstructions of extended trochanteric osteotomies involve the union of a much larger segment of bone than a non-extended type of osteotomy. Plate 10 can be utilized in a reconstruction of both an extended trochanteric osteotomy and a non-extended trochanteric osteotomy.

In a method of bone fixation utilizing plate 10, the limb is abducted and the bone segments or pieces are reduced using a reduction clamp (not shown). Such reduction may be about a joint prosthesis, such as a femoral hip prosthesis, such that the bone segments are reduced over the prosthesis (not shown). Plate 10 is placed along a medial aspect of femur 50 just inferior to the lesser trochanter 52 such that the lesser trochanter 52 is at least partially positioned within superior cut-out 34 of plate 10, as illustrated in FIG. 1F. Once in the desired position, bone screws are placed through each bone screw opening 32 and into the bone 50. Such bone screws may be polyaxial bone screws so that they can be oriented at one of a multitude of different angles as desired by the surgeon. Bone screws can also be monolithic, biased, unbiased, serrated and/or self-tapping.

Cables, such as Dall-Miles cables, are preferably pre-threaded through passageways 22 of plate 10 prior to medial placement of the same such that each cable has at least one free end extending from plate 10. As shown in FIG. 1F, beaded cables 60 are threaded through passageways 22 in an inferior to superior direction such that beads 62 of beaded cables 60 are positioned at an inferior end of plate 10. However, it is contemplated that the cables can be threaded to plate 10 in-situ.

Free ends of each cable 60 extending from each passageway 22 are passed over and about a lateral aspect of the trochanteric bone segment, through the anterior abductor muscles, and back to plate 10 where they are threaded through openings 42 in protrusion 40. Such cables 60 are then tensioned until the trochanteric osteotomy or fracture is reduced and rigidly fixed. The cables 60 are secured, such as by crimping protrusion 40, and the remaining free ends of the cables are cut. The resultant construct would include two cables extending horizontally and vertically about the trochanteric bone segment. As can be envisioned from FIG. 1F, the medial placement of plate 10 inferior to lesser trochanter 52 allows cables to be passed over the greater trochanter 54 without interference from a femoral head 56 or neck 58, whether artificial or natural.

However, in other embodiments, depending on the nature of the fracture or osteotomy, only horizontal or only vertical cables through passageways 42 or 22, respectively, may only be utilized. For example, for an extended trochanteric osteotomy, two cables may be passed circumferentially about the femur, as illustrated in FIG. 1F, without them being routed up and over the greater trochanter. This may be beneficial in cases with poor bone quality. The use of plate 10 would distribute the cable tension over a greater area than just cables without plate 10 which could dig in and damage the bone. In some procedures where further securement is desired, bone openings may be drilled through the bone inferior to the bone segment to be rejoined. Cables extending through vertical passageways 22 may then passed over the greater trochanter 54 and down through bone openings about the trochanteric bone segment. In still further embodiments, cables can be routed through both plate 10 at a medial side of a femur, as shown in FIG. 1F, and also through a second bone plate placed at a lateral side of femur, such as a standard lateral bone plate.

Fixation plate 10 can vary in many ways. The following describes many of such variations which are exemplified in the following embodiments. In this regard, the following fixation plate embodiments are generally similar to fixation plate 10 and utilized in the aforementioned method in a similar fashion except where explicitly stated or illustrated otherwise. As such, like elements are accorded like reference numerals but within a higher number series.

Figure 2A:
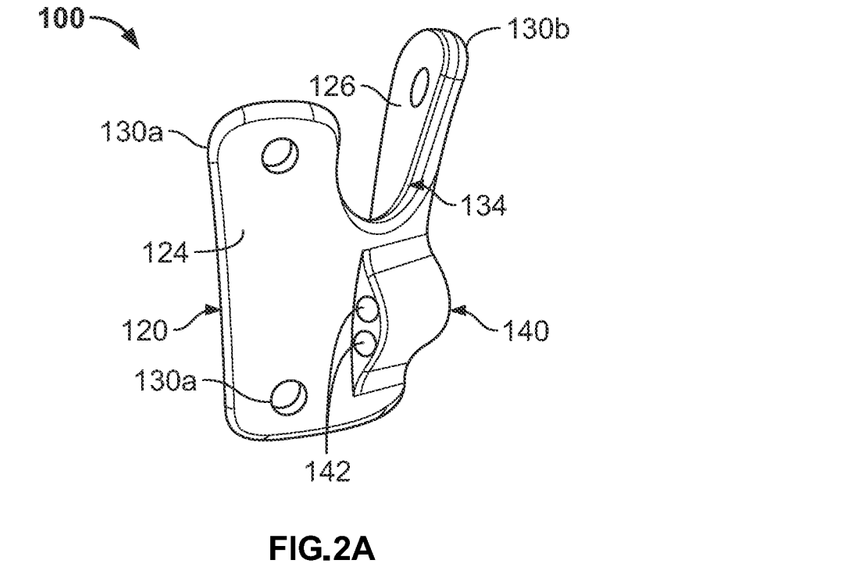
FIG. 2A is a rear perspective view of a fixation plate according to a second embodiment of the present disclosure.
Figure 2B:
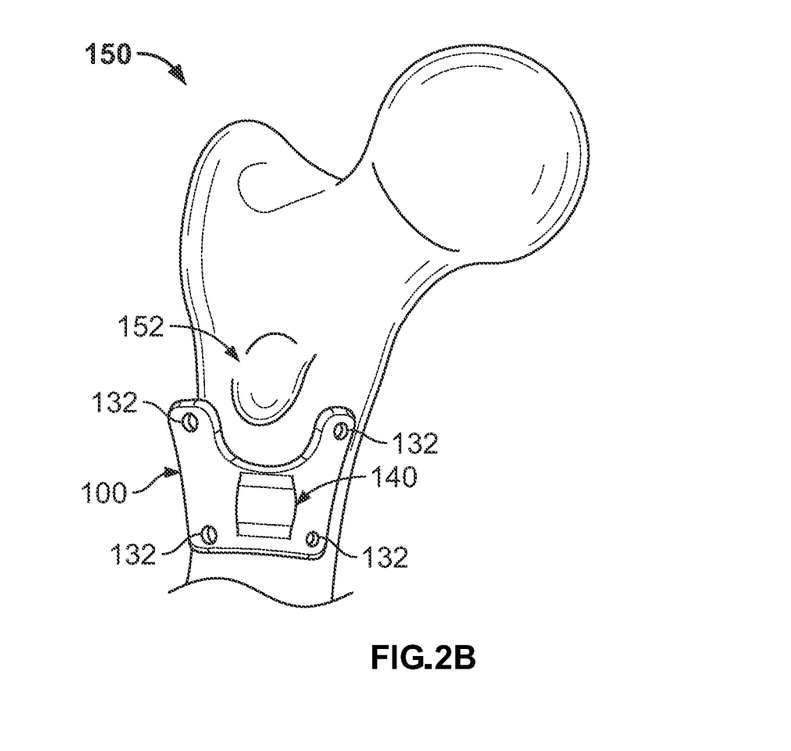
FIG. 2B depicts the fixation plate of FIG. 2A in associate with a proximal femur.

FIGS. 2A-2B depict bone plate 100. Bone plate 100 is similar to bone plate 10 in that it includes front 126 and back sides 124, a body 120, appendages 130a-b extending from body 120, and a cable protrusion 140. In addition, plate 100 includes bone screw openings 132 extending through plate 100 and cable passageways 142 extending side to side through protrusion 142. However, plate 100 differs from plate 10 in that it has two appendages 130a-b, rather than four. Nonetheless, plate 100 has four bone screw openings 132 where two of such bone screw openings extend through appendages 130a-b, respectively, and two extend through opposite sides of body 120. In this regard, plate 120 does not have side cut-outs, such as cut-outs 36. In addition, plate 100 does not have vertical passageways, such as passageways 22, extending through body 120. As shown in FIG. 2B, plate 100 would be similarly positioned inferior to a lesser trochanter 152 of a femur in a method of fixation as plate 10 such that the lesser trochanter 152 is at least partially received within superior cut-out 134.

Figure 3A:
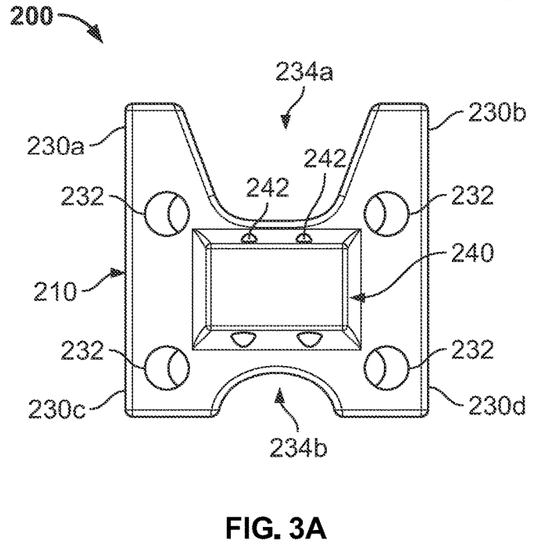
FIG. 3A is a rear elevational view of a fixation plate according to a third embodiment of the present disclosure.
Figure 3B:
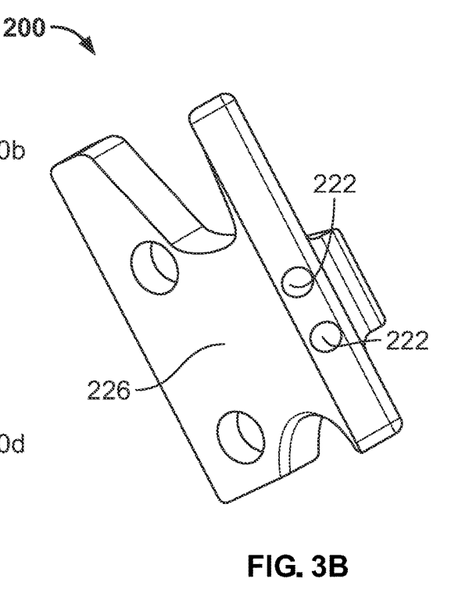
FIG. 3B is a front perspective view of the fixation plate of FIG. 3A.
Figure 3C:
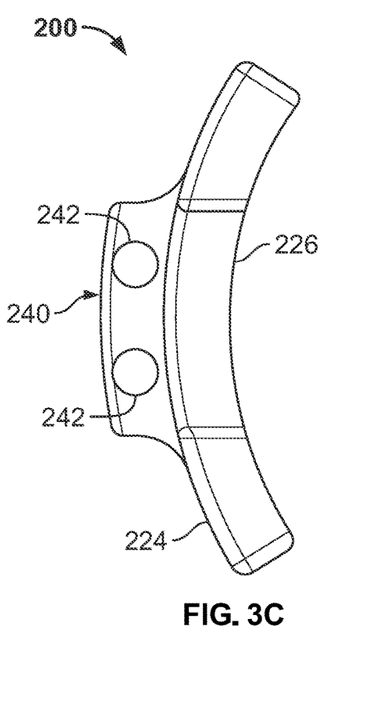
FIG. 3C is a top view of the fixation plate of FIG. 3A.

FIGS. 3A-3C depict bone plate 200. Bone plate 200 is similar to bone plate 10 in that it includes back and front sides 224, 226, a body 220, appendages 230a-d extending from body 220, and a cable protrusion 240. In addition, plate 200 includes bone screw openings 232 extending through plate 200, cable passageways 242 extending through protrusion 240, and cable passageways 222 extending through body 220. However, bone plate 200 differs in that it does not have side cut-outs, but does include an inferior cut-out 234b in addition to superior cut-out 234a. Also, passageways 222 extend through body 220 side to side while passageways 242 extend vertically through protrusion 240. In this regard, superior and inferior cut-outs 234a-b align with passageways 242 so that cables extending therethrough are not impinged by body 220. Thus, in a method of bone fixation, cables horizontally wrapping about the bone segments extend through passageways 222 of body 220, while cables wrapping vertically about the bone segments extend through passageways 242 of protrusion 240.

Figure 3D:
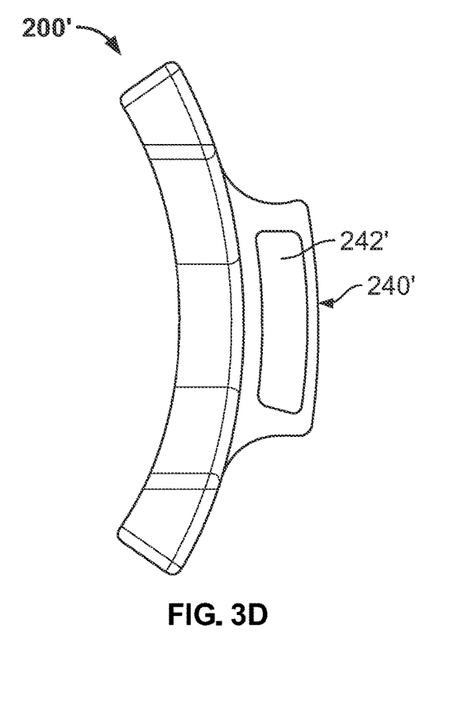
FIG. 3D is a top view of an alternative embodiment of the plate of FIG. 3A.

FIG. 3D depicts plate 200' which is a variation of plate 200. Plate 200', while also including a cable protrusion 240', includes a singular cable passageway 242' extending therethrough as opposed to more than one cable passageway like that of plate 200. Such singular cable passageway 242' is dimensioned to receive more than one cable therethrough.

Figure 4:
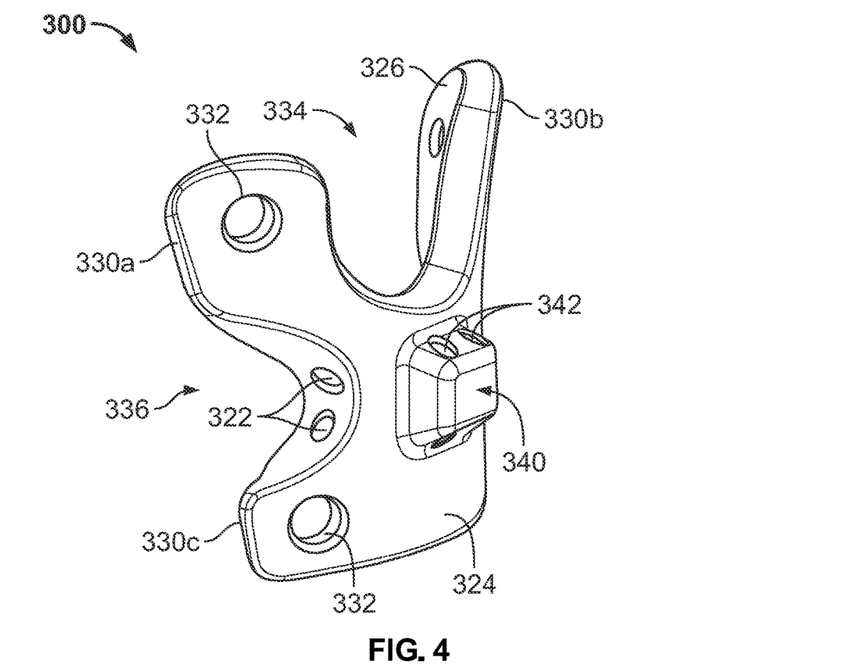
FIG. 4 is a rear perspective view of a fixation plate according to a fourth embodiment of the present disclosure.

FIG. 4 depicts bone plate 300. Bone plate 300 is similar to bone plate 10 in that it includes back and front sides 324, 326, a body 320, appendages 330a-d extending from body 320, and a cable protrusion 340. In addition, plate 300 includes bone screw openings 332 extending through appendages 330a-d and cable passageways 342 extending through protrusion 340. Moreover, plate 300 includes a superior cut-out 334 between first and second appendages 330a-b and opposing side cut-outs 336 between first and third appendages 330a, 330c and second and fourth appendages 330b, 330d, respectively. However, plate 300 differs from plate 100 in a similar fashion as that of plate 200. In this regard, passageways 342 extending through protrusion 340 extend vertically, rather than side to side, and passageways 322 extending through body 320 extend side to side, rather than vertically in a superior-inferior direction. Also, passageways 322 intersect side cut-outs 336.

Figure 5:
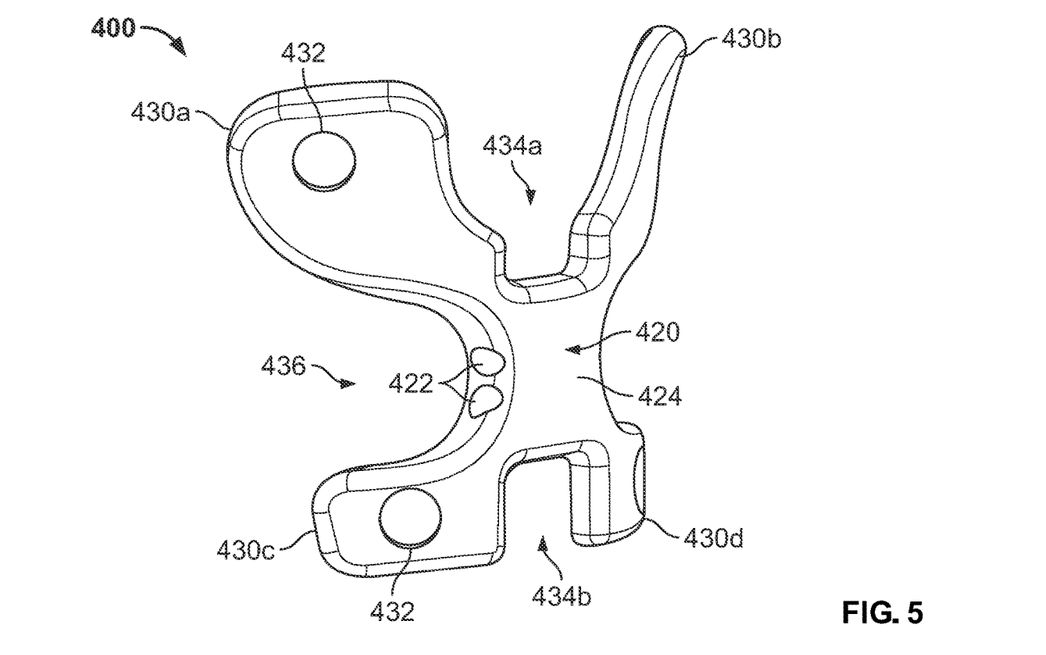
FIG. 5 is a rear perspective view of a fixation plate according to a fifth embodiment of the present disclosure.

FIG. 5 depicts bone plate 400. Bone plate 400 is similar to bone plate 10 in that it includes back and front sides 424, 426, a body 420, and appendages 430a-d extending from body 420. In addition, plate 400 includes bone screw openings 432 extending through appendages 430a-d and cable passageways 422 extending through body 420. However, plate 400 does not include a cable protrusion. Also, cable passageways 422 extend through body 420 side to side. In this regard, plate 400 is a low profile plate 400 in so far as it does not have any protrusion extending from the back side 424 thereof. Plate 400 also includes an inferior cut-out 434b in addition to a superior cut-out 434a and side cut-outs 436.

The following embodiments are also similar to plate 10. However, instead of incorporating bone screw openings for bone screw fixation to a bone, such embodiments utilize spikes or prongs to engage bone and provide initial fixation to prohibit plate migration.

Figure 6:
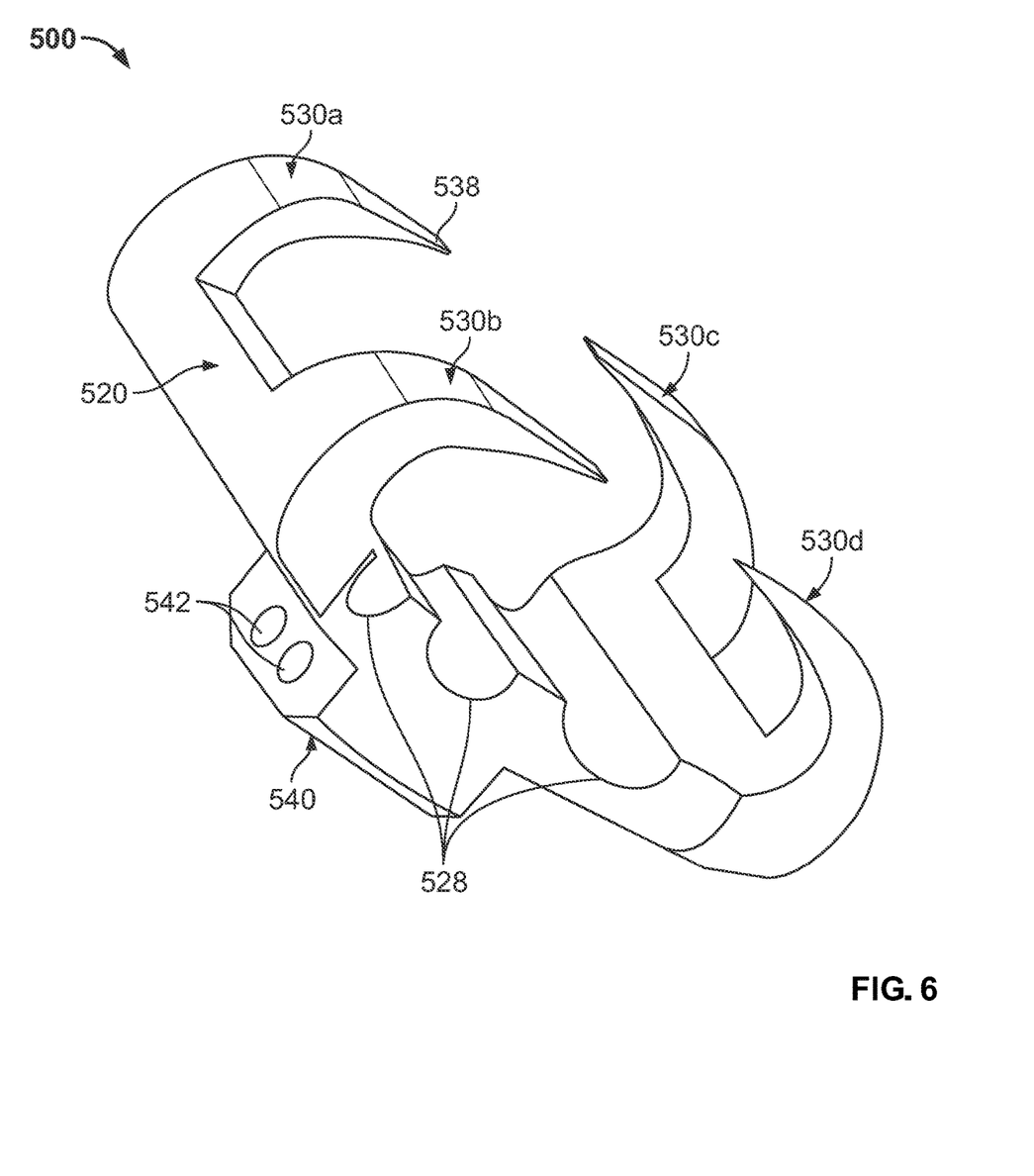
FIG. 6 is a perspective view of a fixation plate according to a sixth embodiment of the present disclosure.

FIG. 6 depicts bone plate 500. Bone plate 500 is similar to bone plate 10 in that it includes a body 520, appendages 530a-d extending from body 520, and a cable protrusion 540. In addition, cable protrusion 540 includes cable passageways 542 extending therethrough. However, unlike plate 10, plate 500 includes prongs or spikes 538 at the ends of each appendage 530. Moreover, appendages 530a-d extend outwardly from body 520 and from each other and then curve back in a direction toward each other such that spikes 538 of a pair of appendages 530 generally face a corresponding spike 538 of an opposing pair. For example, a first pair includes first and second appendages 530a-b and a second pair includes third and fourth appendages 530c-d. The spike 538 of first appendage 530a faces the spike 538 of third appendage 350c while the spike 538 of second appendage 530b faces the spike 538 of fourth appendage 530d. Body 520 also includes a plurality of ribs 528 extending along a bone facing side thereof. Such ribs 528 act as hinges that give the body flexibility so that the first pair of spiked appendages 530a-b can move relative to the other pair 530c-d like a claw. In this regard, appendages 530a-d can rotate relative to body 520. This creates spring-like structure in which the claw comprised of appendages 530a-d can be held in an open position and then released so that the natural bias of body 520 causes the spiked appendages 530a-d to move toward each other and grip whatever bone is positioned therebetween.

Thus, in use, plate 500 may be held open in a first position and then placed against the bone adjacent to a lesser trochanter where it is released so that appendages 530a-d move to a second position in which the spikes 538 of appendages 530a-b are positioned closer to appendages 530c-d than in the first position thereby gripping the bone to prohibit migration of plate 500. Plate 500 can be placed onto the bone such that passageways 542 extend horizontally in a manner similar to passageways 42 when plate 10 is secured to femur 50. However, plate 500 can also be placed onto a femur such that passageways 542 extend vertically in a similar manner to passageways 242 of plate 200.

Figure 7A:
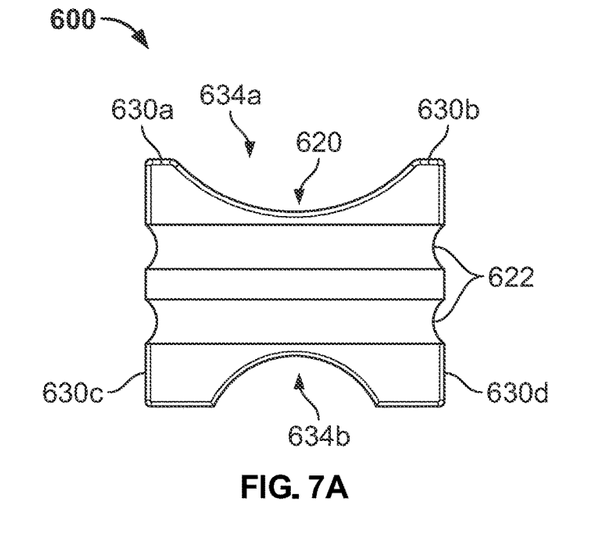
FIG. 7A is a rear elevational view of a fixation plate according to a seventh embodiment of the present disclosure.
Figure 7B:
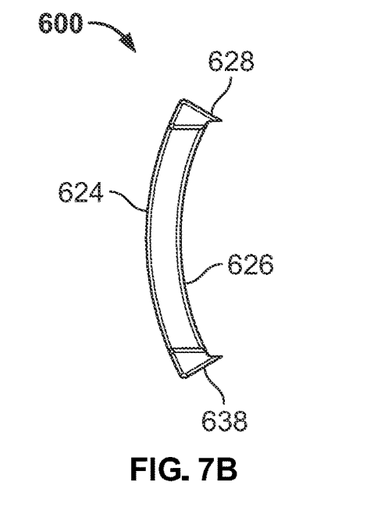
FIG. 7B is a side elevational view of the fixation plate of FIG. 7A.
Figure 7C:
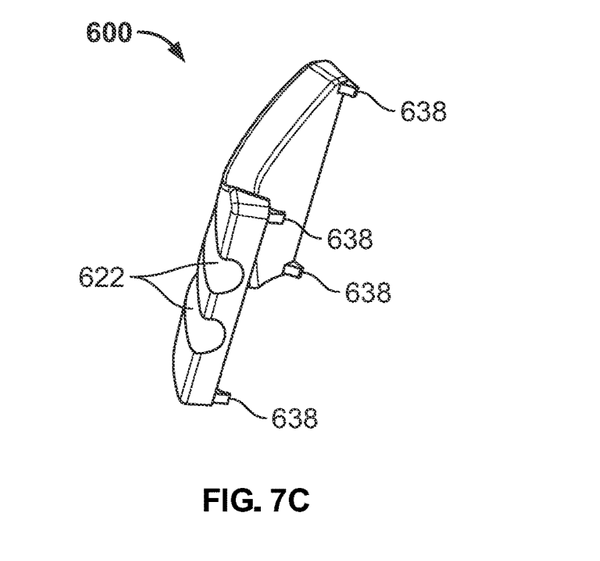
FIG. 7C is a side perspective view of the fixation plate of FIG. 7A.

FIGS. 7A-7C depict bone plate 600. Bone plate 600 is similar to bone plate 10 in that it includes a front side 626, a back side 624, a body 620 and appendages 630*a-d* extending from body 620. In addition a first and second appendage 620*a-b* are separated by a superior cut-out 634*a*, and third and fourth appendages 630*c-d* are separated by an inferior cut-out 634*b*. However, unlike plate 10, a spike 637 extends frontward from each appendage 630*a-d* in lieu of a bone screw opening. Moreover, unlike plate 500, spikes 638 extend straight in a backward direction and generally do not face each other. Plate 600 also does not include a cable protrusion or any passageways extending through body 620 like that of plate 10. Instead, plate 600 has a plurality of grooves 622 extending along the back side 624 thereof and in a side to side direction transverse to the superior-inferior direction. In the embodiment depicted, plate 600 has two of such grooves 622. However, more or less grooves 622 are contemplated depending on how many cables are utilized for reconstruction. Grooves 622 are configured to receive cables therein so as to help retain cables and prevent migration of the cables during the healing process.

Grooves 622 allows cables to be wrapped about bone segments prior to placement of plate 600. In this regard, in a method of bone fixation, cables can be wrapped horizontally about a proximal femur as previously described with respect to plate 10. Plate 600 may then be placed against the femur at a medial aspect thereof and adjacent to a lesser trochanter. The cables can then be aligned with a respective groove 622 and tightened so that the cables are received within their respective groove 622. As each cable is tensioned, the tensile force of such cables press the plate 600 tightly against the femur so that spikes 638 dig into the bone which helps prevent migration of the plate 600 and, consequently, the cables themselves since they are retained by grooves 622 of plate 600.

Plate 600 can have various spike configurations. For example, spikes 638 shown in FIGS. 7A-7C are wedge shaped projections that have sharpened ends that help cut into a femoral cortex. Bone plate 600 may have a roughened surface at the front side 626 thereof that may abut the bone once spikes 638 are engaged in order to enhance migration resistance.

Figure 7D:
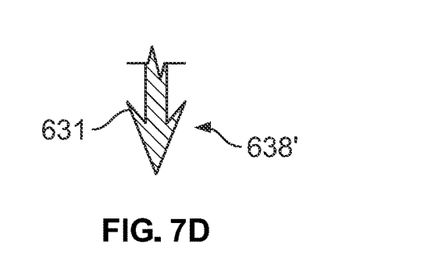
FIG. 7D is a schematic of an alternative spike of the fixation plate of FIG. 7A.
Figure 7E:
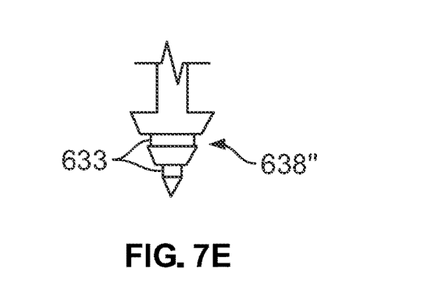
FIG. 7E is a schematic of another alternative spike of the fixation plate of FIG. 7A.

FIGS. 7D and 7E depict other spike configurations. Spike 638' of FIG. 7D includes a backwardly projecting hook or barb 631 which catches on the bone once fully seated within the bone to prevent backing out of spike 638'. Spike 638" of FIG. 7E includes circumferential grooves 633 extending thereabout. Such grooves 633 facilies bone migration therein during the healing process which helps prevent spike from backing out of the bone.

Figure 8A:
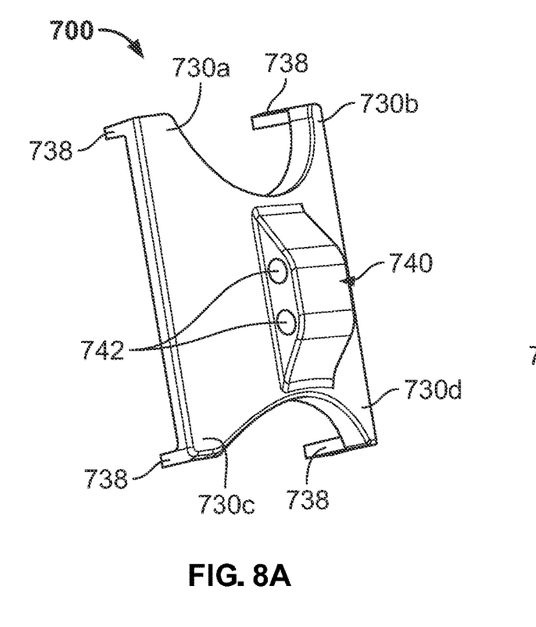
FIG. 8A is a rear perspective view of a fixation plate according to a ninth embodiment of the present disclosure.
Figure 8B:
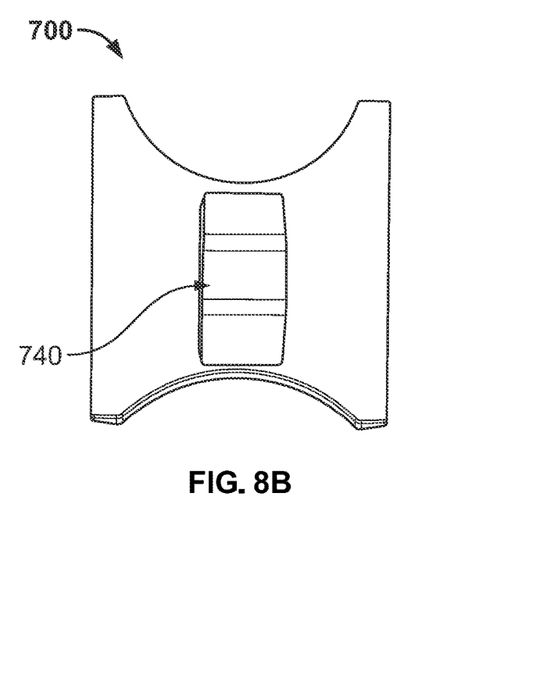
FIG. 8B is a rear elevational view of the fixation plate of FIG. 8A.

FIGS. 8A and 8B depict bone plate 700. Bone plate 700 is similar to bone plate 10 in that it includes a body 720 and appendages 730*a-d* extending from body 720. In addition, bone plate 700 includes a cable protrusion 740 extending backwardly therefrom that includes cable passageways 742 that extend in a side to side direction. However, unlike plate 10, appendages 730*a-d* each have a spike extending frontwardly therefrom. Such spikes may be the same as those described above with regard to plate 600.

Figure 9A:
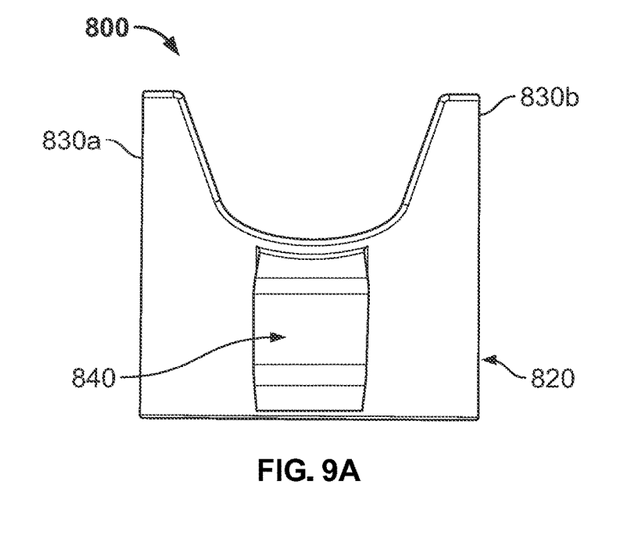
FIG. 9A is a rear elevational view of a fixation plate according to a tenth embodiment of the present disclosure.
Figure 9B:
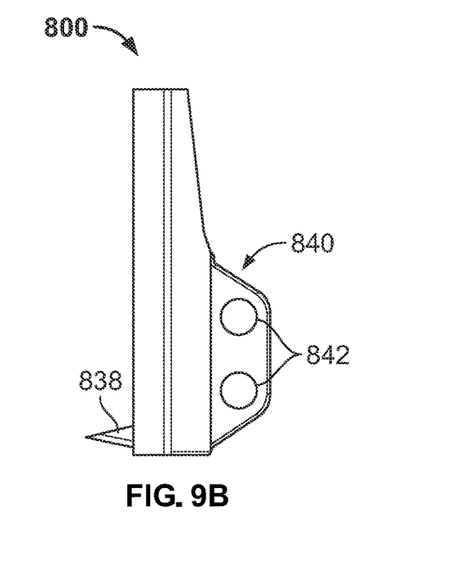
FIG. 9B is a side elevational view of the fixation plate of FIG. 9A.

FIGS. 9A and 9B depict a bone plate 800. Bone plate 800 is similar to bone plate 10 in that it includes a body 820, appendages 830*a-b* extending from body 820, and a cable protrusion 840. In addition, plate 800 includes cable passageways 842 extending side to side through protrusion 842. However, plate 800 differs from plate 10 in that it has two appendages 830*a-b*, rather than four. Also, instead of bone screw openings, plate 800 includes a pair of spikes 838 extending frontwardly from plate 800 at an inferior end thereof. This differs from the previous spiked plates 500, 600, and 700 in that only two spikes are provided. However, as previously discussed, plate 800 would be placed adjacent a lesser trochanter such that at least a portion of the lesser trochanter would be positioned between appendages 830*a-b*. This relationship relative to lesser trochanter helps prevent migration of plate in a superior direction. The addition of spikes 838 helps prevent migration in other directions as well.

Figure 10:
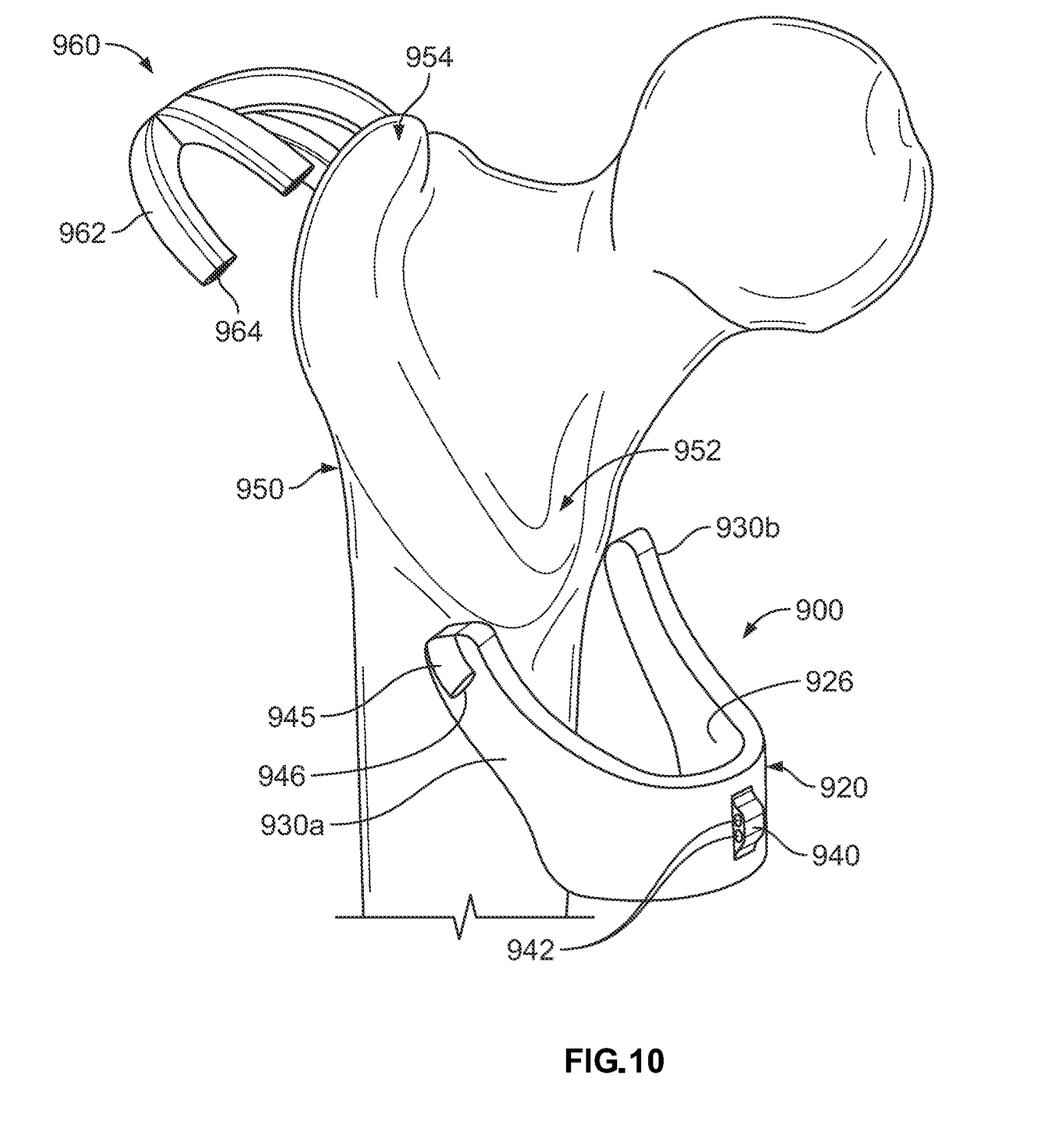
FIG. 10 depicts a fixation plate system according to an embodiment of the present disclosure and in association with a proximal femur.

FIG. 10 depicts a bone fixation system according to an embodiment of the present disclosure. Bone fixation system includes a medial fixation plate 900 and a lateral crown or brace 960. Plate 900 is similar to other plates previously described herein in that it has a body 920 with a concave bone facing surface 926 and appendages 93*a-b* extending from body 920. In addition, plate 900 has a cable protrusion 940 with passageways 942 extending side to side therethrough. However, unlike in the other embodiments, appendages 930*a-b* also include cable protrusions 945 with their own passageways 946 such that cables may be routed through the passageways 942, 946 of protrusions 940, 945 of appendages 940 and body 920. This configuration helps direct and stabilize the cables wrapping about a bone, such as femur 950.

Crown 960 is comprised of multiple arms 962 that depend downwardly to form an open umbrella shape or semispherical shape. In this regard, crown 960 is configured to be placed over the greater trochanter 954 so that arms 962 extend in a generally inferior direction. Each Arm 962 includes at least one passageway or channel 964 extending entirely therethrough and along its entire length. Crown 960 and plate 900 operate in conjunction with each other such that they each provide solid, stable structures to prevent cable slippage and migration over an extended period of time as the bone fragments heal.

In use, body 920 of plate is positioned inferior to lesser trochanter 950 of femur 900 so that appendages extend superiorly and cradle lesser trochanter 952. The positioning of the lesser trochanter 952 between arms 930*a-b* prohibits migration of plate 900 in a superior direction. Crown 960 is placed over greater trochanter 954 so that its arms 962 extend inferiorly toward plate 900, as shown. Cables may be preloaded through passageways 942, 946, 964 of both plate 900 and crown 960 so that once plate 900 and crown 960 are respectively positioned at the lesser and greater trochanters 952, 954, then cables can be tightened to secure the assembly. However, in other embodiments, cables can be threaded through plate and crown in-situ.

Figure 11:
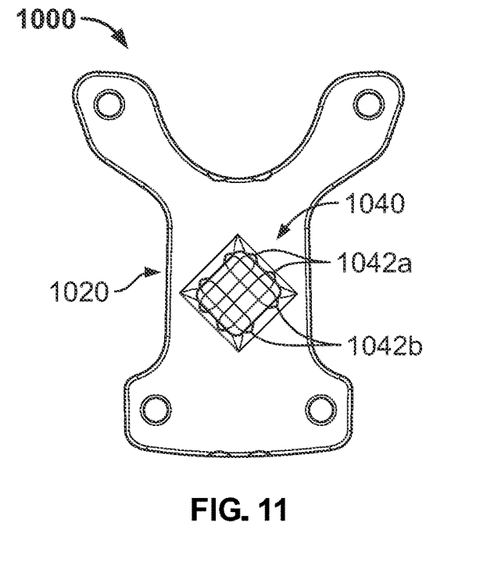
FIG. 11 is a front view of a fixation plate according to a twelfth embodiment of the present disclosure.

FIG. 11 depicts bone plate 1000. Bone plate 1000 is similar to bone plate 10 except that protrusion 1040 includes four passageways 1042 rather than two. In addition, such passageways 1042 are differently oriented compared to passageways 42. In this regard, plate 1000 includes a first pair of passageways 1042*a* and a second pair of passageways 1042*b*. First pair of passageways 1042*a* intersect the second pair of passageways 1042*b*. In other words, each passageway 1042 defines a central axis and the central axes of the first pair of passageways 1042*a* intersect the central axes of second passageways 1042*b*, as illustrated in FIG. 11. Such intersection preferably occurs at a perpendicular angle. However, other angles, such as 30, 45, and 60 degrees, are contemplated. In addition, both pairs of passageways 1042*a-b* extend in both an inferior-superior direction and a transverse direction. This arrangement allows either the first or second pair of passageways 1042*a-b* to be utilized during a procedure depending on the circumstances of the procedure. For example, first pair of passageways 1042*a* may be utilized in conjunction with one or more cables in a procedure on a left femur while second pair of passageways 1042*b* may be utilized in a procedure on a right femur.

Figure 12A:
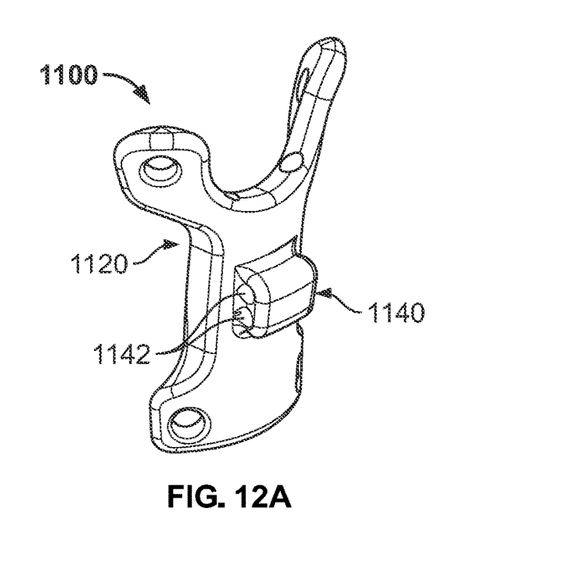
FIG. 12A is side perspective view of a fixation plate according to a thirteenth embodiment of the present disclosure.
Figure 12B:
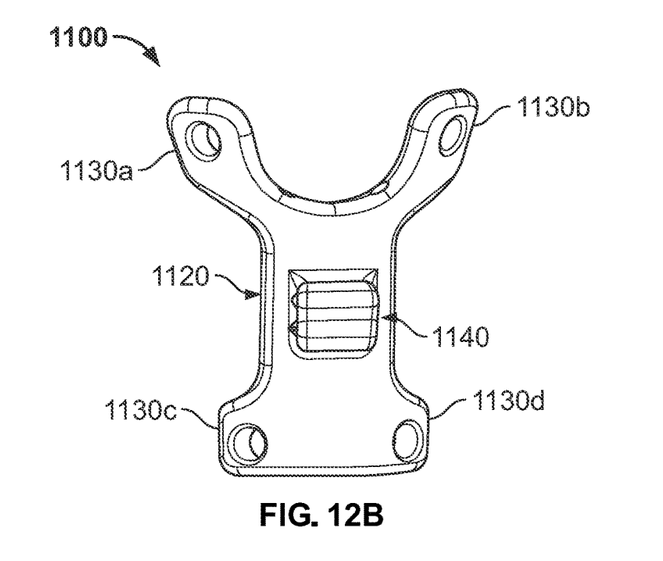
FIG. 12B is a front view of the fixation plate of FIG. 12A.

FIGS. 12A and 12B depict bone plate 1100. Bone plate 1100 is similar to bone plate 10 except that plate 1100 has an extended body as compared to plate 10. In other words, plate 1100 has a greater superior-inferior length than plate 10. In addition, while not shown, protrusion 1140 may be longer in the superior-inferior direction than protrusion 40 so that passageways 1142 are placed further apart than passageways 42 in plate 10. However, in the embodiment depicted, protrusion 1140 is identical to protrusion 40.

Figure 13:
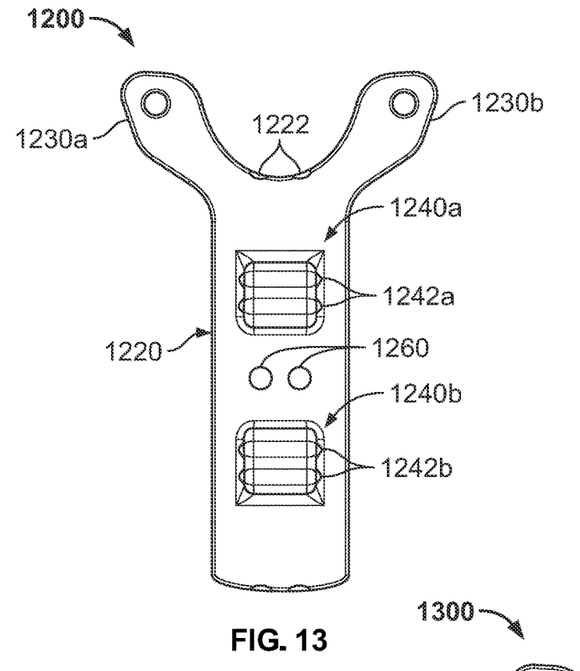
FIG. 13 is a front view of a fixation plate according to a fourteenth embodiment of the present disclosure.

FIG. 13 depicts bone plate 1200. Bone plate 1200 is similar to bone plate 10 in that it includes first and second appendages 1230*a-b* extending from a body 1220. However, plate 1200 does not include third and fourth appendages. Although, it is contemplated that some embodiments of plate 1200 may include third and fourth appendages. Plate 1200 also differs in that body 1220 is longer than body 20 and includes first and second cable protrusions 1230*a-b* extending from body 1220. Such protrusions 1240*a-b* are similar to protrusion 40 in that they each include a respective pair of passageways 1240*a* and 1242*b* extending in a transverse direction. Protrusions 1240*a-b* are separated from each other in a superior-inferior direction. A pair of through-openings 1260 are located between protrusions 1240*a-b* and extend through body 1220 from an outer surface to an inner surface thereof. Such through-openings 1260 may intersect with openings 1222, which extend through plate 1200 along a length thereof, or may be arranged so that they do not intersect with each other. Such through-openings 1360 can each receive a cable, such as a beaded cable. The configuration of plate 1200, and even plate 1100, can be utilized in cases where multiple cable fixation options are desirable and/or where the bone pieces intended to be secured exist over a great length of the bone, such as in the case of extended osteotomies and fractures that are located beyond the trochanter.

Figure 14:
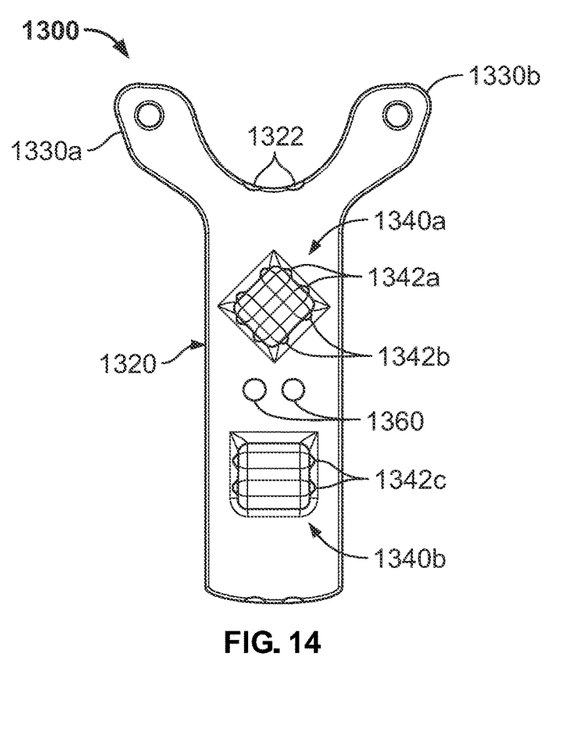
FIG. 14 is a front perspective view of a fixation plate according to a fifteenth embodiment of the present disclosure.

FIG. 14 depicts bone plate 1300. Bone plate 1300 is similar to bone plate 1200 in that it includes first and second cable protrusions 1340*a-b* extending from body 1320 and through-holes 1360 extending through body 1320 between protrusions. However, plate 1330 differs in that that first cable protrusion 1340*a* is configured like protrusion 1040 of plate 1000. In this regard, protrusion 1340*a* is diamond shaped and has two pairs of intersecting passageways 1342*a-b* which are oriented at oblique angles relative to a longitudinal axis of plate 1300.

The exemplary fixation plates and like hardware described herein may be formed layer-by-layer using an additive layer manufacturing (ALM), i.e., 3D printing, process so no separate connection mechanism is necessary to bring together any of the components of such implants. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901 as well as U.S. Patent Publication No. 2006/0147332, each of which is hereby incorporated by reference in their entireties herein. Other methods of ALM, which can be used to form the herein described implants, include stereolithography (SLA), fused deposition modeling (FDM), and continuous liquid interface production (CLIP).

When employing powder-bed based technologies, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology.

Each layer of the above described implants may be constructed from biocompatible metals, such as but not limited to any one of or any combination of titanium and its alloys, stainless steel and its alloys, magnesium and its alloys, cobalt and its alloys including a cobalt chrome alloy, nickel and its alloys, silver, tantalum, and niobium. Additionally, a combination of materials may be incorporated into the herein described implants.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of bone fixation, comprising:
   placing a bone plate adjacent to a lesser trochanter on a medial aspect of a femur such that at least a portion of the lesser trochanter is positioned between appendages of the bone plate, the appendages each having a first end connected to a body of the bone plate and extending to a second end thereof;
   wrapping a first cable extending from the body of the bone plate and between the first and appendages about a first and second bone fragment of a proximal end of the femur; and
   tightening the first cable to secure the first and second bone fragments together.

2. The method of claim 1, further comprising cutting the femur to form the first and second segments of the femur.

3. The method of claim 1, further comprising securing the bone plate to the femur via one of bone screws and bone spikes.

4. The method of claim 1, further comprising positioning bone of the femur between spiked ends of the appendages, and moving the appendages from a first position to a second position such that the spiked ends of the appendages engage the bone to secure it thereto.

5. The method of claim 1, further comprising threading the first cable through first and second passageways extending through the body of the bone plate.

6. The method of claim 5, further comprising threading a second cable through a third passageway of the bone plate and about the proximal femur.

7. The method of claim 6, wherein the third passageway extends through a protrusion extending from a back side of the body of the bone plate.

8. The method of claim 7, wherein the third passageway extends side-to-side transverse to a superior-inferior direction.

9. The method of claim 7, wherein the third passageway extends in both a superior-inferior direction and in a direction transverse to the superior-inferior direction.

10. The method of claim 7, further comprising threading a third cable through a fourth passageway of the bone plate.

11. The method of claim 10, wherein the fourth passageway extends through the body of the bone plate.

12. The method of claim 11, wherein the third and fourth passageways extend side-to-side transverse to a superior-inferior direction.

13. The method of claim 6, wherein the first and second passageways are oriented parallel to each other.

14. The method of claim 1, wherein the bone plate includes a bone facing surface being roughened.

15. The method of claim 1, wherein the placing step includes positioning the body of the bone plate inferior to the lesser trochanter.

16. A method of reconstructing a proximal end of a femur, comprising:
    positioning a first bone segment comprising a greater trochanter of the femur against a second bone segment of the femur;
    placing a bone plate at a medial aspect of the femur adjacent to a lesser trochanter of the femur such that a body of the bone plate is positioned inferior relative to the lesser trochanter and appendages of the bone plate extend superiorly therefrom;
    wrapping a first cable extending in a superior direction from the body of the bone plate about the first and second bone segments of the proximal femur and back to the bone plate; and
    tightening the first cable to secure the first and second bone segments together.

17. The method of claim 16, further comprising securing the bone plate to the femur via one of bone screws and bone spikes.

18. The method of claim 16, further comprising cutting the femur to form the first and second segments of bone.

19. The method of claim 16, wrapping a second cable extending from the body of the bone plate about the proximal femur in a direction transverse to a superior-inferior direction.

20. The method of claim 16, wherein both a first end and a second end of the cable are positioned inferior to the lesser trochanter after the cable is wrapped around the first and second bone segments and tightened to secure the first and second bone segments.

* * * * *